United States Patent [19]
Hollander

[11] Patent Number: 6,162,053
[45] Date of Patent: Dec. 19, 2000

[54] ANALOG DENTAL WRENCH

[75] Inventor: Bruce L. Hollander, Boca Raton, Fla.

[73] Assignee: Biolok International Inc., Deerfield Beach, Fla.

[21] Appl. No.: 09/432,376

[22] Filed: Nov. 1, 1999

[51] Int. Cl.[7] .................................................. A61C 3/00
[52] U.S. Cl. .............................. 433/141; 81/481; 81/483
[58] Field of Search ................................. 433/141, 173, 433/174; 81/467, 478, 480, 481, 483

[56] References Cited

U.S. PATENT DOCUMENTS

| | | |
|---|---|---|
| 2,512,032 | 6/1950 | Mellert . |
| 2,972,271 | 2/1961 | Gill . |
| 3,018,677 | 1/1962 | Mutolo et al. . |
| 3,633,445 | 1/1972 | Aijala . |
| 5,129,823 | 7/1992 | Hughes ..................................... 433/141 |
| 5,152,200 | 10/1992 | Kaplan ........................................ 81/478 |
| 5,337,638 | 8/1994 | Coss et al. .................................. 81/483 |
| 5,366,412 | 11/1994 | Beaty et al. ............................. 483/174 |
| 5,503,042 | 4/1996 | Larson et al. .............................. 81/478 |
| 6,007,336 | 12/1999 | Sapkos ..................................... 433/141 |
| 6,021,694 | 2/2000 | Beger ......................................... 81/483 |

*Primary Examiner*—Ralph A. Lewis
*Attorney, Agent, or Firm*—M K Silverman

[57] ABSTRACT

There is provided an analog dental torque wrench in which, at a given level of torque imparted to a dental work object, force communicated by a compression spring through an interface impart against a ball bearing will cause rotation of a handle and medial hollow cylindrical segment of the wrench off of the bearing to an off-axis position relative to a longitudinal work axis, disabling a wrench head, precluding further application of a torque to the work object, and causing shear of the wrench to occur either to the left or right of the longitudinal axis, and external to the mouth of the patient.

3 Claims, 2 Drawing Sheets

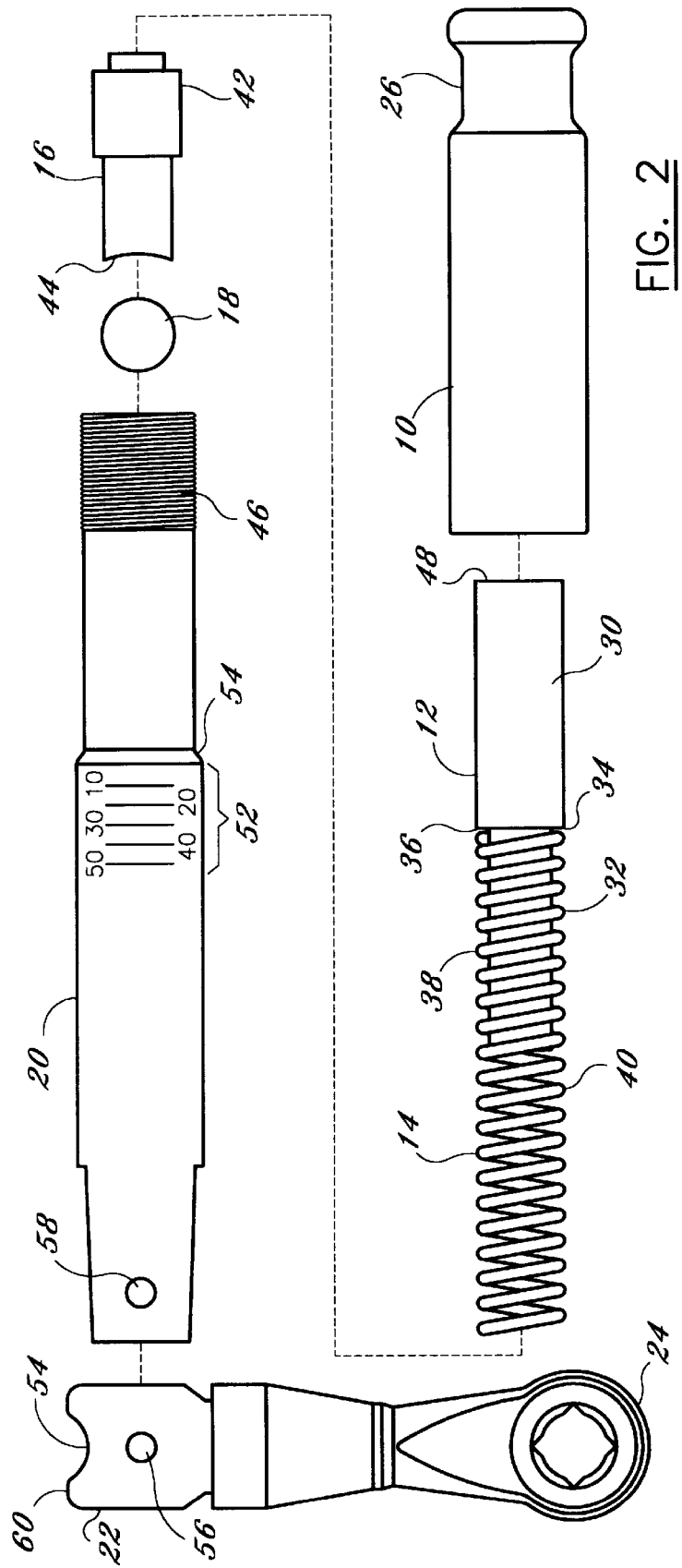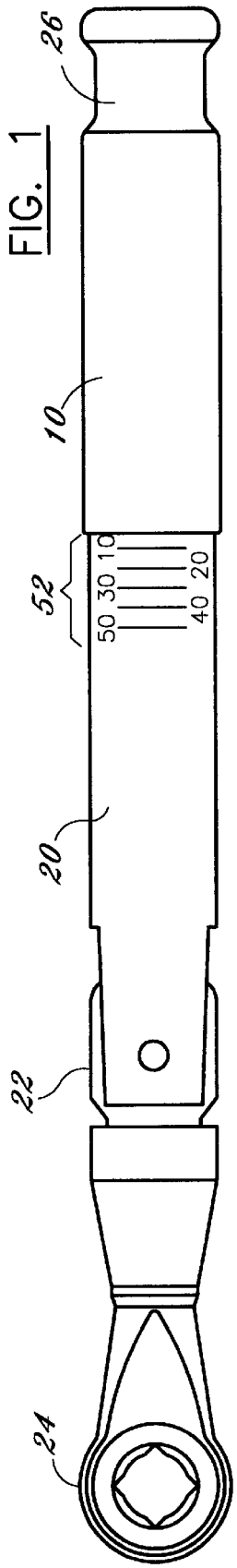
FIG. 1
FIG. 2

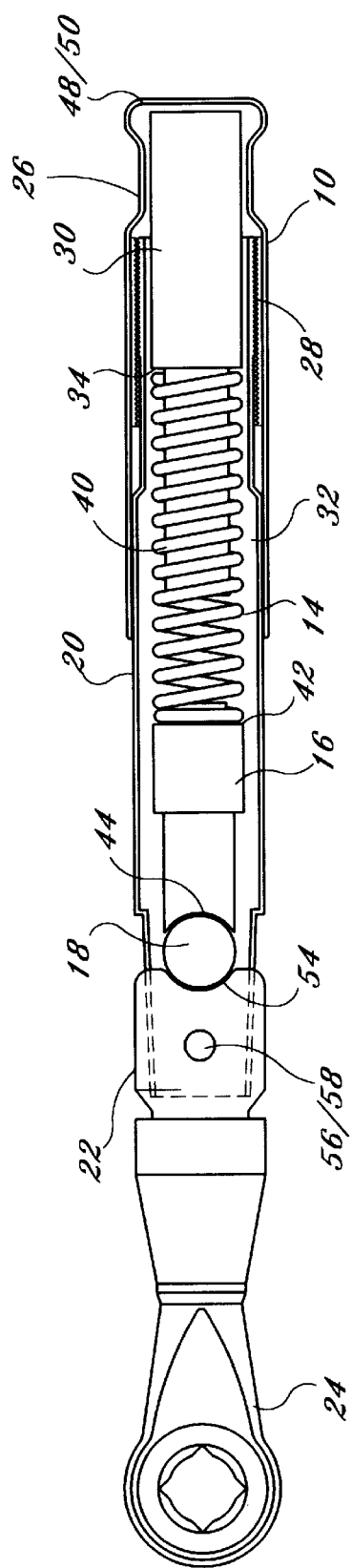
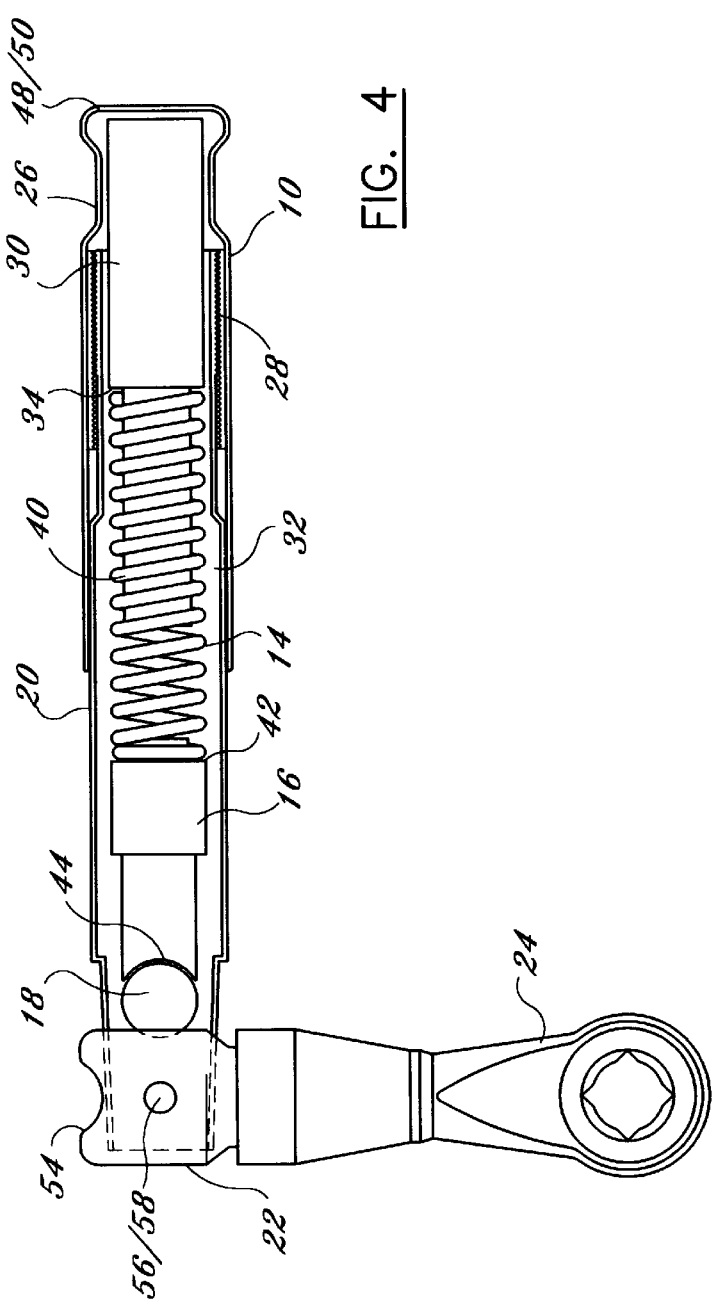

6,162,053

ANALOG DENTAL WRENCH

APPLICATION FOR LETTERS PATENT

BE IT KNOWN THAT I, Bruce L. Hollander a resident of the State of Florida, and a citizen of the United States of America, have invented a certain new and useful improvement in an Analog Dental Wrench, of which the following is a Specification:

BACKGROUND OF THE INVENTION

A long-standing problem in the area of dental and medical wrenches and, more particularly, in the area of dental torque ratchet wrenches, has been that of assuring that excessive force or torque, or less than what is specified is not advertently applied to an implant or abutment employed in a dental implant procedure. The same concern, relative to limiting of torque transmitted to a work object, exists in other areas involving delicate mechanical assembly in orthodontics and maxillofacial surgery.

In addition to the long standing need in the prior art for a torque-limiting dental and medical wrench has been the fact that, to the extent of their existence in the prior art, such wrenches have been digital in nature, that is, limit the torque that can only be controlled, i.e., one wrench, one torque setting. Accordingly, if the safest or most desirable maximum torque in a given application falls between one of the digital or incremental levels at which such a torque wrench can be set, a decision then must be made as to whether to operate the tool at a torque shear either below or above the level at which the dentist or technician would have desired.

A further problem, addressed by the present invention, is that of providing a dental torque or ratchet wrench having a sufficiently low profile to be comfortably used within the very close clinical spaces which are available in implant procedures in the mouth or in the body in orthopedic applications.

The prior art, as known to the within inventors, is represented by U.S. Pat. No. 5,129,823 (1992) to Hughes, entitled Driver Tool and Method for Implant Dentistry; and U.S. Pat. No. 5,366,412 (1994) to Beaty, et al, entitled Torque Limiting Clutch and its Uses. Further, the Dentsply Corporation is believed to offer and sell a low profile dental torque ratchet wrench. The Dentsply product is, however, not an analog system but, rather, is one, which employs a mechanical fuse to disable the driver head of the tool when a preset force is imparted thereto.

The inventors are also aware of other prior art which, particularly, included U.S. Pat. No. 2,512,032 (1950) to Mellert, entitled Yielding Torque Indicating Tool; U.S. Pat. No. 3,018,677 (1962) to Mutulo, entitled Cartridge-Type Spring Bias Means for Predetermined Torque Release Wrench; and U.S. Pat. No. 5,152,200 (1992) to Kaplan, entitled Torque Signaling Wrench. The instant system of the inventors differs from this art in a number of material ways, including the capacity of the present wrench to be readily re-calibrated by the clinician at chairside to accommodate implant placement, restorative requirements (10–20 newton-centimeters) and abutment placement (30–40 newton-centimeters). For example, said reference to Mellert is capable of only limited calibration and cannot be calibrated to the range of 20 to 40 newton-centimeters which is the range within which most implant dentistry occurs.

The reference to Mutulo does not employ a ball bearing as the means of defining the shear point of the system. Also Mutulo cannot be recalibrated and does not provide a complete shear or off axis break. As such, Mutulo cannot be utilized in any dental application.

The within inventive wrench provides for a range of calibration of between 10 and 70 Newton centimeters with formal settings provided at 10, 20, 30, 70 or specified newton-centimeters. Also, the instant wrench will break either to the left or right, a consideration of importance to a left handed dentist and where implant work is being done upon the upper teeth.

The instant improved Adjustable Analog Dental Torque Wrench differs, inter alia, from the above referenced art in that the location of the break or shear point is external to the mouth of the patient, the extent of off-axis shear so achievable is much greater than that in any prior art, and the symmetry of such shear point may be either to the left or right of the axis thereby rendering the present wrench useful to a dentist who is either left or right handed.

With respect to this latter feature, a wrench which is bi-directionally torque limiting which is not the case in any art of record. For example, U.S. Pat. No. 5,337,638, to Cos teaches a uni-directional torque-limiting wrench in which, as well, the break of the handle relative to the wrench head will occur in or near to the mouth of the patient. Such would constitute a hazardous factor if the wrench of Cos were used in such a clinical context.

The same is the case in regard to the U.S. Pat. No. 2,972,271 to Gill in which the shear point of the device would, if used in a dental context, occur in or near the mouth of the patient. In addition, the structure of Gill does not afford a sharp definition of when a torque limit has been reached in the use of the tool.

To the knowledge of the within inventors, only said U.S. Pat. No. 5,152,200 to Kaplan teaches use of a ball bearing in a torque limit sensing means, located at or near the center of the wrench. However, the pivot point thereof, that is, the point of attachment of the wrench head to the wrench handle, is so far removed in the location of the ball bearing thereof that Kaplan, while apparently bi-directional in its shear and torque sensing, is only capable of off-axis rotation in a range of 10 to 15 degrees. This is not a sufficient rotational shear to afford adequate safety in clinical dental environment. context. Accordingly, the prior art, however viewed, does not teach a bi-directional, substantially off-axis shear, and out-of-the-mouth shear, adjustable, analog torque wrench, usable for medical and dental purposes.

SUMMARY OF THE INVENTION

The instant invention relate s to an analog dental wrench having selectable torque-shear limits in which the wrench comprises discrete components which include a hollow cylindrical barrel handle having an axial length including an interior surface having spiral threading thereupon. An elongate preferably cylindrical member is axially secured within said handle and extends substantially beyond said length thereof. A hollow medial cylindrical segment defines an extended longitudinal axis co-linear with the longitudinal axis of said barrel handle and said elongate member, said hollow cylindrical segment having a spiral threading complemental to that of said barrel housing upon a proximal surface thereof, and further having torque level indicia described upon a surface distally of said threading, said threaded portion of said hollow medial segment proportioned for slip-fittable insertion within said barrel handle. Further provided is a linear constant force compression spring proportioned for insertion against a proximal annular radial surface of said elongate member secured within said barrel housing. Therein, rotation of said barrel upon said threadings of said medial segment defines means for selectable incremental compression of said spring by rotational advance of said annular surface of said elongate member against a proximal end of said spring. Further provided are interface means proportioned for conformal engagement, at a proximal surface thereof, with a distal end of said spring and, at a distal surface of said interface means, with one side of a ball bearing. Said interface means is axially symmetric relative to the longitudinal axis of said medial segment, elongate member, and barrel handle. Further provided is a ball arm having a surface proportioned for conformal frictional engagement with an opposite side of said ball bearing, said ball arm including a pivot point common in location to a pivot point within a distal end of said medial segment, thereby rendering said ball arm pivotally dependent therefrom. Said common pivot point is situated near to said conformal engagement surface of said ball arm. There is further provided a wrench head assembly integrally distally dependent from said ball arm, at an opposite end from said ball bearing engagement surface, in which a combined axial length of said ball arm and said wrench assembly comprises between about 30 and about 60 percent of the total length of the inventive wrench. Rotation of said handle and medial cylindrical segment will, in addition to imparting torque to the wrench head, impart torque to said frictional engagements between said ball bearing, and said interface means and ball arm respectively. At a given level, such imparted torque will overcome, force communicated by said compression spring through said interface means against said ball bearing, thereby causing rotation of said handle and medial hollow cylindrical segment off of said bearing to an off-axis position relative to said longitudinal axis, disabling said wrench head assembly, precluding further application of torque to a work object, and causing shear of the wrench to occur either to the left or right of said longitudinal axis, and external to the mouth of a patient.

It is an object of the invention to provide an adjustable torque limiting analog wrench having particular application in the area of implant dentistry and medicine.

It is another object to provide a dental wrench of the above type capable of analog adjustment of the shear or torque limit level of the wrench.

It is a further object of the invention to provide a tool of the above type having a low profile particularly suitable for use in clinical spaces, applicable to implant dentistry and orthopedics.

It is a still further object to provide a general purpose torque limiting analog wrench.

It is a yet further object of the invention to provide an adjustable dental torque wrench capable of pre-defined torque level shear to either the left or right of the axis of the handle thereof, and external to the mouth of a patient.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

FIG. 1 is an external assembly view of the inventive analog dental wrench.

FIG. 2 is an exploded view showing the each of the constituent element thereof.

FIG. 3 is an assembly breakaway view in which the handle and medial cylindrical segment have been removed to show the internal relationship of the elements of the invention.

FIG. 4 is a view, similar to the view of FIG. 3, however showing a 90-degree off-axis position of the wrench head and ball arm relative to the handle and medial cylindrical segment.

DETAILED DESCRIPTION OF THE INVENTION

With reference to the exploded view of FIG. 2, the present analog dental wrench may be seen to include a cylindrical barrel handle 10, an elongate member 12, a linear constant force compression spring 14, interface means 16, a ball bearing 18, a hollow medial cylindrical segment 20, a ball arm 22, and a wrench head assembly 24. These parts are shown, in assembly, in the views of FIGS. 1 and 3.

It is noted that the axial length of elongate member 12 is substantially greater than the axial length of barrel handle 10.

Barrel handle 10 is characterized by circumferential convex gripping surface 26 and spiral threadings 28 (see FIG. 3) formed upon an interior surface thereof.

Elongate member 12 includes a proximal portion 30 and a distal portion 32 having a reduced diameter relative to the proximal section. At the interface between said portions 30 and 32 is an annular radial surface 34 which function to secure and stabilize proximal end 36 of spring 14. As may be noted in FIGS. 2 and 3, a proximal segment 38 of spring 14 is positioned about distal portion 32 of elongate member 12 while a distal segment 40 of spring 14 rests against a proximal annular radial surface 42 of interface means 16 which surface defines the distal extent of movement of spring 14 in the fashion that said annular surface 34 of elongate member 12 defines the proximal extent of spring 14.

At a distal side of interface means 16 is a convex surface 44 which is proportioned for substantially conformal engagement with a proximal side of said ball bearing 18.

With reference to the assembly views of FIGS. 1 and 3, it may be appreciated that hollow medial cylindrical segment 20 includes a threaded proximal portion 46 which is complemental to threading 28 within barrel handle 10. Thereby, handle 10 is proportioned for slip-fittable insertion about threaded portion 46 of medial segment 20. Thereby, given the abutment of surface 48 of proximal portion 30 of elongate member 12 against interior proximal radial end 50 of handle housing 10, spring 14, when positioned between annular surfaces 34 and 42, will be incrementally axially compressible by the effect of selectable rotational advance of said barrel handle 10 upon its threaded interface with threaded portion 46 of medial cylindrical segment 20. Accordingly, by selectable rotation, or counter-rotation, of handle 10 relative to medial segment 20, the degree of force of spring 12 upon interface means 16 and, thereby, imparted across convex surface 44 to ball bearing 18, may be accurately controlled. More particularly, indicia 52 are provided near the center of cylindrical segment 20, immediately distally of shoulder 54. These indicia reflect values of torque used in implant dentistry which represents a safe or acceptable limits of torque which can be safely applied to a work object within the mouth of a patient, e.g., a dental implant, abutment, or screw associated with the same. Accordingly, a dental torque wrench, to be safely usable by an implant dentist, must shear or break off axis, and safely out and from the mouth of the patient if an indicated level of torque is exceeded. Accordingly, with the present inventive analog torque wrench, it is not necessary for a dentist to purchase a different wrench for each different torque level that may be applicable to a given procedure or given type or brand of a component used within an implant system. Also, given the complete axial symmetry of the system as described herein, it is not necessary for a dentist to purchase a torque wrench on the basis of whether he is left or right handed.

With further reference to the assembly view of FIG. 3, ball arm 22 may be seen to include a surface 54 proportioned for conformal frictional engagement with a distal side of said ball bearing 18. Further, ball arm 22 includes a pivot point 56 comprising a pivot point common to pivot point 58 of medial cylindrical segment 20. It is, thereby, to be appreciated that ball arm 22 includes pivot point 56 which is common with pivot point 58 of distal end of the medial segment 20 to thereby render said pivot art 22 pivotally dependent therefrom. Further, and of substantial importance to the functionality of the present invention, said common pivot points 56 and 58 exist near to ball bearing 18, that is, the respective centers of said pivot points and said ball bearing are less than five ball bearing diameters from each other. This proximity of pivot point 58/66 to ball bearing 18 has been found to be essential to achieving both a shear point sufficiently far from wrench head 24 to avoid the mouth of a patient and to assure that a 90 degree shear of the type shown in FIG. 4 can be effected.

As may be further noted in the figures, wrench head assembly 24 is integrally distally dependent from ball arm 22. Therein, it is noted that the ratio of the combined length of wrench head assembly 24 and ball arm 22 to the entire length of the analog wrench is in a range of 30 to 60 percent thereof. This ratio, in addition to the above discussed proximity of pivot point 56/58 to ball bearing 18, assures that the break or pivot point of the analog wrench will occur outside of the patient thereby rendering the wrench suitable for use within the clinical spaces applicable to implant dentistry.

Summarizing the operation of the present system, rotation of the handle and medial cylindrical segment will impart pressure to wrench head 24 and, internally to the wrench, will impart torque to the frictional engagements which exist between both convex surface 44 of interface means 16 and conformal surface 54 of ball arm 22 against ball bearing 18. When the selected level of pressure caused by the force of compression spring 14 is reached (see torque indicia 52) the handle and medial cylindrical segment rotate off of bearing 18 to a substantial off-axis position as is shown in FIG. 4. This is enabled through the particular arcuate curvature of arm 60 of the ball arm 22. Accordingly, ball bearing 18, during the shear process, is able to slip over conformal surface 54 and arm 60 of the ball arm 22 to permit the wrench head assembly 24 to shear, either to the right or left, off of the system axis into the 90 degree position shown in FIG. 4. Thereby, what is achieved is a complete or total shear of the wrench head assembly relative to the handle of the system, thereby assuring that not only will the break point occur safely outside of the mouth of the patient but, as well, that the shear or break is substantially great enough to assure complete safety to the patient.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

Having thus described my invention, what I claim as new, useful and non-obvious obvious and, accordingly, secure by Letters Patent of the United States is:

1. An analog dental wrench with selectable adjustable torque-shear limits, the wrench comprising:

(a) a cylindrical barrel handle having an axial length and including proximal interior surface having spiral threadings thereupon, (b) an elongate member axially secured within said handle and extending substantially beyond said axial length thereof;

(c) a hollow medial cylindrical segment defining an extended longitudinal axis, having a proximal portion including spiral threading thereupon complemental to said threadings of said interior surface of said barrel handle, and having torque level indicia inscribed upon an outer surface of said cylindrical segment located distally of said threading, said threaded portion proportioned for slip fittable insertion within said barrel handle;

(d) a linear constant force compression spring proportioned for insertion against a proximal annular radial surface of said elongate member and within said medial cylindrical segment, in which rotation of said barrel handle upon said threadings of said medial segment defines means for selectable incremental axial compression of said spring by rotational advance of said annular radial surface of said elongate member thereagainst;

(e) interface means proportioned for conformal engagement, at a proximal surface thereof, with a distal end of said spring and, at a distal surface of said interface means, with a proximal side of a ball bearing, in which said interface means is axially symmetric about said longitudinal axis of said medial segment;

(f) a ball arm having a surface proportioned for conformal frictional engagement with a distal side of said ball bearing, said ball arm including a pivot point common to a pivot point within a distal end of said medial segment, thereby rendering said ball arm pivotally dependent therefrom, said common pivot point situated near to said conformal engagement surface of said ball arm, wherein said ball arm is symmetric about said longitudinal axis of said medial segment; and (g) a wrench head assembly integrally distally dependent from said ball arm at an opposite end thereof from said ball bearing engagement surface, whereby, rotation of said handle and medial cylindrical segment will impart torque to said wrench head assembly and will also impart torque to said frictional engagements between said ball bearing and said interface means and ball arm, respectively as such that, at levels defined by the degree of compression of said compression spring, force imparted by said compression spring, through said interface means and against said ball bearing, will be overcome, thereby causing rotation of said handle and medial cylindrical segment off of said ball bearing to an off-axis position relative to said wrench head assembly, the same to preclude further application of torque to a work object, and causing shear of the wrench head assembly to occur either to the left or right of said wrench head assembly and externally of a mouth of a patient.

2. The analog dental wrench as recited in claim 1 in which a combined length of said ball arm and said wrench assembly comprises between about 30 and about 60 percent of the total length of said analog wrench.

3. The wrench as recited in claim 2 in which said common pivot point of said ball arm and said distal end of said medial cylindrical segment define a location relative to a center of said ball bearing of less than five ball bearing diameters.

* * * * *